United States Patent
Tsubota et al.

[11] Patent Number: 5,876,200
[45] Date of Patent: Mar. 2, 1999

[54] DENTURE PRODUCING DEVICE

[75] Inventors: Tomoyuki Tsubota, Hakodate; Tadashi Kimura, Kurashiki, both of Japan

[73] Assignee: Sankin Kogyo Kabushiki Kaisha, Japan

[21] Appl. No.: 864,740

[22] Filed: May 29, 1997

[30] Foreign Application Priority Data

Jun. 28, 1996 [JP] Japan ................................. 8-187005

[51] Int. Cl.$^6$ ................................................ A61C 11/00
[52] U.S. Cl. .............................................. 433/59; 433/56
[58] Field of Search ..................................... 433/56, 59

[56] References Cited

U.S. PATENT DOCUMENTS

| | | | |
|---|---|---|---|
| 1,498,559 | 6/1924 | Lightcap | 433/56 |
| 1,518,075 | 12/1924 | Kesling | 433/56 |
| 2,200,058 | 5/1940 | Chott | 433/59 |
| 2,608,761 | 9/1952 | Scott | 433/59 |
| 3,200,497 | 8/1965 | Goodfreind | 433/56 |
| 3,423,834 | 1/1969 | Irish | 433/59 |
| 4,762,490 | 8/1988 | Ludwigs | 433/59 |
| 5,176,515 | 1/1993 | Andrews | 433/24 |
| 5,348,471 | 9/1994 | Notomi | 433/56 |

FOREIGN PATENT DOCUMENTS 59-40848   3/1984   Japan.

Primary Examiner—Cary E. O'Connor
Attorney, Agent, or Firm—Lorusso & Loud

[57] ABSTRACT

A working model for a lower jaw is disposed on the bottom of an articulator, a pair of support rods are disposed on both sides of the articulator so as to extend upward from the bottom of the articulator, a pair of joint portions are provided on top of the paired support rods to support both end portions of a shaft, a working model for an upper jaw is mounted to that shaft to permit movement of the upper working model relative to the lower working model, a pair of side pins are disposed at upper, right and left, outside positions of artificial teeth mounted into the articulator, and a tooth aligning device is mounted to the side pins. Further, a center pin is mounted along the midline of the articulator, and holding portions for mounting the tooth aligning device are formed on the support rods and the center pin.

4 Claims, 8 Drawing Sheets

DENTURE PRODUCING DEVICE

BACKGROUND OF THE INVENTION

The present invention relates to a denture producing device wherein a pair of support rods are disposed on both sides of an articulator, and joint portions using ball bearings are provided on top of the support rods, thereby permitting three movements of a working model which movements are opening-closing, antero-posterior, and lateral movements.

According to the conventional method usually adopted for tooth arrangement, pre-fabricated-teeth are arranged tooth by tooth manually.

A denture aligning device has been proposed as a device for assisting the manual tooth arrangement in Japanese Patent Laid-Open No. 59-40848. In this proposed device, the positions of artificial teeth are determined by operating a large number of adjusting screws.

However, the denture aligning device proposed in the Japanese Patent Laid-Open No. 59-40848 is disadvantageous in that the operation of many adjusting screws requires time equal to or longer than the time required in manual operation unless the worker is a skilled person of a considerably high level.

Furthermore, in the Japanese Patent Laid-Open No. 59-40848, there is made no reference to gum forming.

On the other hand, in the conventional articulator wherein all the operations are performed manually, a center pin is mounted along the midline and puts obstacles at the time of arrangement of the anterior teeth. This is inconvenient. For example, the worker cannot see the anterior teeth directly. Further, the movement of instruments is restricted.

SUMMARY OF THE INVENTION

It is an object of the present invention to provide a denture producing device which permits a worker to make a denture alignment conforming to the shape and size of each patient's teeth even if the worker is not a skilled person.

In the denture producing device of the present invention, which is an improvement over the conventional device, a pair of support rods are disposed on both sides of an articulator, and joint portions are provided on top of the support rods, thereby permitting motions of working models.

According to a typical example of the denture producing device of the present invention, a working model for the lower jaw is disposed on the bottom of an articulator, a pair of support rods are disposed on both sides of the articulator so as to extend upward from the bottom of the articulator, a pair of joint portions using ball bearings are provided on top of the paired support rods to support both end portions of a shaft, and a working model for the upper jaw is mounted on that shaft, thereby permitting opening and closing, as well as three movements—anterior, posterior and lateral— movements, of the upper working model relative to the maxillary working model. The present invention is not limited to this type of a denture producing device. For example, the present invention also includes improvements over a mean value articulator not using ball bearings (Approval No. 54B 1111) and a semi-adjustable articulator (Approval No. 05B 1015).

According to a denture producing device in one typical aspect of the present invention, a center pin is mounted along the midline of an articulator, and a support member for supporting an artificial teeth aligning device and for setting it at a desired vertical position is provided at the top of the articulator to which is mounted a working model for the upper jaw.

A preferred example of the support member comprises side pins. Holding portions for mounting an artificial teeth aligning device are formed on at least one of support rods and the center pin so that the artificial teeth aligning device is supported at least at three points by the side pins and at least one of the support rods and the center pin. For example, the artificial teeth aligning device is supported at least at three points by holding portions of a pair of side pins and a holding portion of the center pin. Further, the artificial teeth aligning device is supported at least at three points by holding portions of a pair of support rods and a holding portion of the center pin.

According to a denture producing device in another aspect of the present invention, for mounting an artificial teeth aligning device, a pair of side pins are disposed at positions, for example, right and left outside of the upper jaw of artificial teeth mounted in an articulator. Preferably, the side pins are disposed outside the first premolars on the right and left sides of the upper jaw.

In both denture producing devices referred to above, it is preferable that in the transition region from the lingual region of artificial teeth to the gingival region, gum forming is performed on the palatal or lingual side by the affixing of a pre-fabricated pattern.

Preferably, an aligning device for receiving therein such artificial teeth as anterior teeth and molar teeth (e.g. upper anterior teeth and lower molar teeth) which are reference teeth in tooth alignment is attached to an articulator with working models already mounted thereto, and molten wax is allowed to flow therein to form a standard alignment of anterior teeth and molar teeth (e.g. upper anterior teeth and lower molar teeth) and their gingiva partially.

Alignment of the lower anterior teeth and upper molar teeth can be done in conformity with the upper anterior teeth and lower molar teeth by a conventional method.

The support member used in the present invention is not limited to the form of side pins. There may be adopted another form insofar as it can support a tooth aligning device at a desired vertical position. The number of side pins is not limited to two.

The tooth aligning device used in the present invention can be formed using any of various materials, including rubber (say silicone rubber), metals and synthetic resins (say plastics).

According to the most suitable form of a tooth aligning device, a cavity is formed in a mold and artificial teeth are mounted into the cavity, provided the invention is not limited to this form.

According to the present invention, a worker can arrange teeth in accordance with the shape and size of teeth of each individual patient.

For example, a standard alignment of upper anterior teeth and lower molar teeth and their partial gum forming can be done by placing pre-fabricated anterior teeth and molar teeth (say upper anterior teeth and lower molar teeth), which are considered to be standard teeth in tooth alignment, into an aligning device, then attaching the aligning device to an articulator of a special construction with working models already mounted thereto, and subsequent flowing of molten wax therein. In this case, minor adjustments of curves for the both upper anterior teeth and lower molar teeth can be done in accordance with cases.

In the transition portion from the lingual region of artificial teeth to the gingival region, gum forming on the palatal or lingual side can be done easily by the affixing of a pre-fabricated pattern.

By the above points it is made possible to greatly reduce the working time.

If a support member, for example a pair of side pins, is disposed at right and left outside of the upper jaw of artificial teeth, even removal of the center pin at the midline does not cause a change in occlusal vertical dimension, and thus the anterior teeth aligning operation becomes easier.

BRIEF DESCRIPTION OF THE DRAWINGS

Preferred embodiments of the present invention will be described below with reference to the accompanying drawings, in which.

EMBODIMENTS

Figure 1:
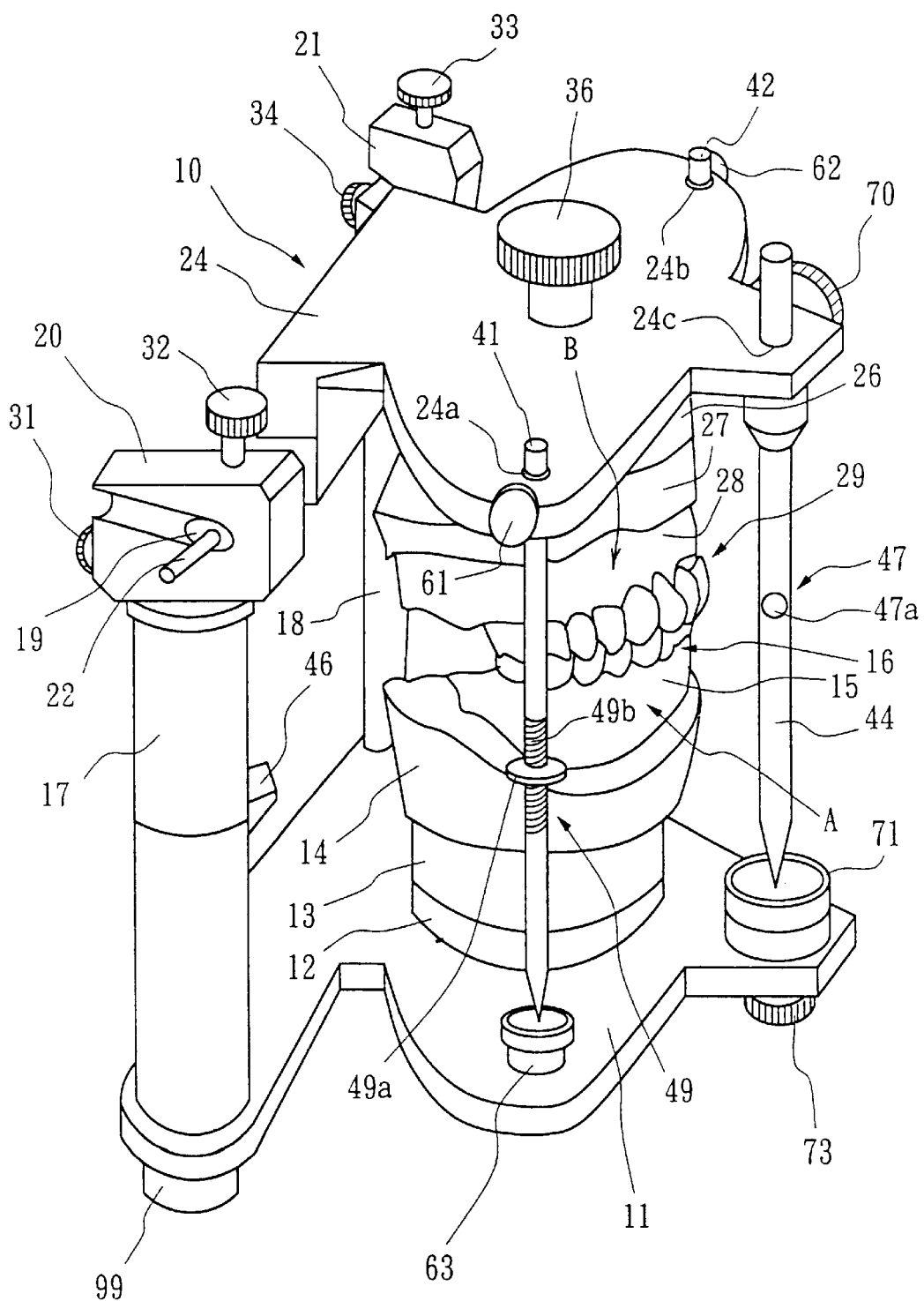
FIG. 1 is a schematic perspective view of a denture producing device according to an embodiment of the present invention.

FIG. 1 shows a denture producing device according to an embodiment of the present invention.

In the state shown in FIG. 1, wax dentures A and B are disposed in an articulator 10. The lower wax denture A is rested on a pedestal 12 through lower working models 13 and 14, while the upper wax denture B is rested on a pedestal 25 through upper working models 26 and 27.

To be more specific, a pair of support rods 17 and 18 are provided on both sides of the articulator 10 so as to extend upward from a bottom member 11 of the articulator. On top of the paired support rods 17 and 18 are provided a pair of joint portions 20 and 21 using ball bearings 19 (only one is shown in FIG. 1). Both end portions of a shaft 22 are supported by the paired joint portions 20 and 21, and a top member 24 of the articulator is fixed to the shaft 22.

In connection with the lower wax denture A, the disc-shaped pedestal 12 is fixed to the upper central part of the bottom member 11 of the articulator 10 removably with a fixing screw 35. The lower working models 13 and 14 are provided in two stages on the upper surface of the pedestal 12. The working models 13 and 14 are provided with an artificial gingiva 15 and a series of artificial teeth 16.

In connection with the upper wax denture B, the disc-shaped pedestal 25 is fixed to the lower central part of the top member 24 of the articulator 10 removably with a fixing screw 36. The upper working models 26 and 27 are provided in two stages on the lower surface of the pedestal 25. The working models 26 and 27 are provided with an artificial gingiva 28 and a series of artificial teeth 29.

The mounted state of the shaft 22 relative to the paired joint portions 20 and 21 is adjusted with adjusting screws 31, 32, 33 and 34, whereby a relative position between the wax dentures A and B can be adjusted. More specifically, the artificial gingiva 28 and a series of artificial teeth 29 of the upper working models 26 and 27 can perform three movements which are opening-closing, antero-posterior, and lateral movements.

As to the construction of the articulator described above, there may be adopted a known construction.

Such components as the support rods 17, 18, bottom member 11 and top member 24 are not limited to those illustrated in the drawings. Various other corresponding components are adoptable.

In the denture producing device of this embodiment, a pair of side pins 41 and 42 are disposed so as to assume right and left outside positions with respect to the upper jaw of artificial teeth 28 of the upper working models 26 and 27. The side pins 41 and 42 have holding portions 49 for the mounting of tooth aligning devices 50 and 51. A center pin 44 is mounted along the midline of the articulator 10. Holding portions 46 for mounting the tooth aligning devices 50 and 51 are formed respectively on both support rods 17 and 18. Further, a holding portion 47 for mounting the tooth aligning devices 50 and 51 is formed on the center pin 44, provided the devices 50 and 51 are not shown in FIG. 1.

The holding portions 49 of the paired side pins 41 and 42 for mounting the tooth aligning devices 50 and 51 are disposed at right and left outside positions of the upper jaw of the artificial teeth 29 mounted in the articulator 10. Preferably, the holding portions 49 of the side pins 41 and 42 are positioned outside the upper, right and left first premolars of the upper wax denture B.

Preferably, for example as shown in FIG. 1, the holding portions 49 of the side pins 41 and 42 can be adjusted in their vertical position by threadedly engaging a small, internally threaded disc 49a with external threads 49b and then turning the disc 49a.

The side pins 41 and 42 are inserted through holes 24a and 24b formed in both sides of the top member 24 of the articulator 10, and extend downward. The side pins 41 and 42 are adjusted in their vertical position by turning adjusting screws 61 and 62. The lower ends of the side pins 41 and 42 are supported easily removably in contact with tray-like support members 63 disposed on both sides of the bottom member 11 of the articulator 10. Bearing surfaces of the support members 63 which support the lower ends of the side pins 41 and 42 can be adjusted in their vertical position by turning the support members 63.

It is preferable that the holding portion 47 of the center pin 44 be positioned outside the upper anterior teeth of the artificial teeth 29 in the upper wax denture B. As shown in FIG. 1 for example, the holding portion 47 of the center pin 44 comprises a small adjusting screw 47a and a through hole (not shown) formed horizontally in the center pin 44 so as to intersect the adjusting screw 47a. The center pin 44 is inserted into a through hole 24c formed in a tip portion of the top member 24 of the articulator 10, and extends downward. The center pin 44 is adjusted in its vertical position by turning an adjusting screw 70. The lower end of the center pin 44 is supported easily removably in contact with a tray-like support member 71 disposed on a tip portion of the bottom member 11. The tray-like support member 71 is secured to the bottom member 11 of the articulator 10 removably with a fixing screw 73.

Like the holding portions 49 of the side pins 41 and 42 and the holding portion 47 of the center pin 44, it is preferable that the holding portions 46, 46 of the paired support rods 17 and 18 for holding the tooth aligning devices 17 and 18 also be located at corresponding outside horizontal positions laterals of the artificial teeth 29 of the upper wax denture B as mounted in the articulator 10. Though not shown, like the tray-like support members 63, the tooth aligning device bearing surfaces of the holding portions 46, 46 can also be adjusted in their vertical position.

Three legs 99 are provided on the lower surface of the bottom member 11.

In the present invention various tooth aligning devices are employable, but in the illustrated embodiment two types of tooth aligning devices 50 and 51 are used.

Figure 4:
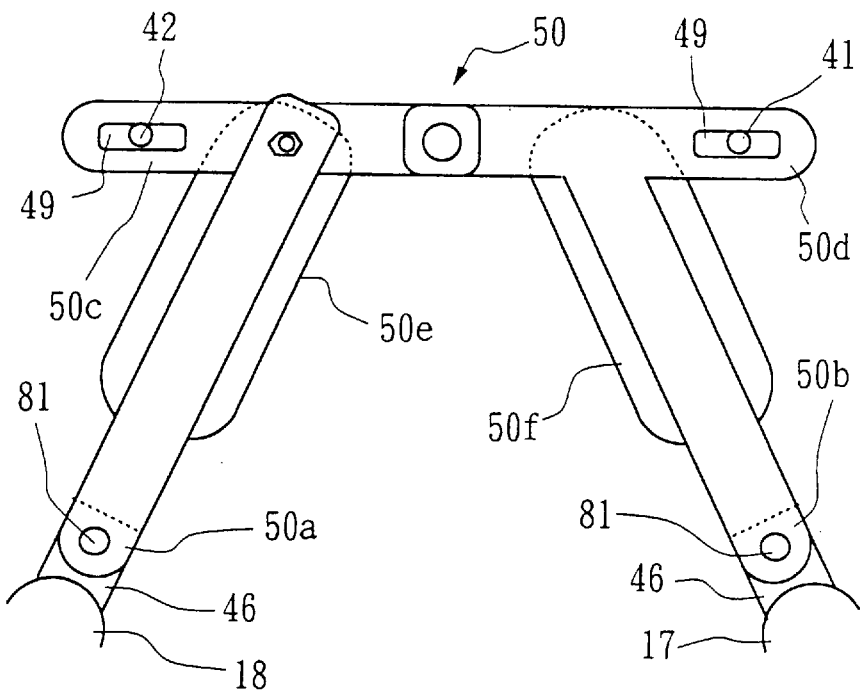
FIG. 4 is a schematic top view of an aligning device for mandible molar teeth to be used in the denture producing device, showing the aligning device in a reversed and partially omitted state.
Figure 8:
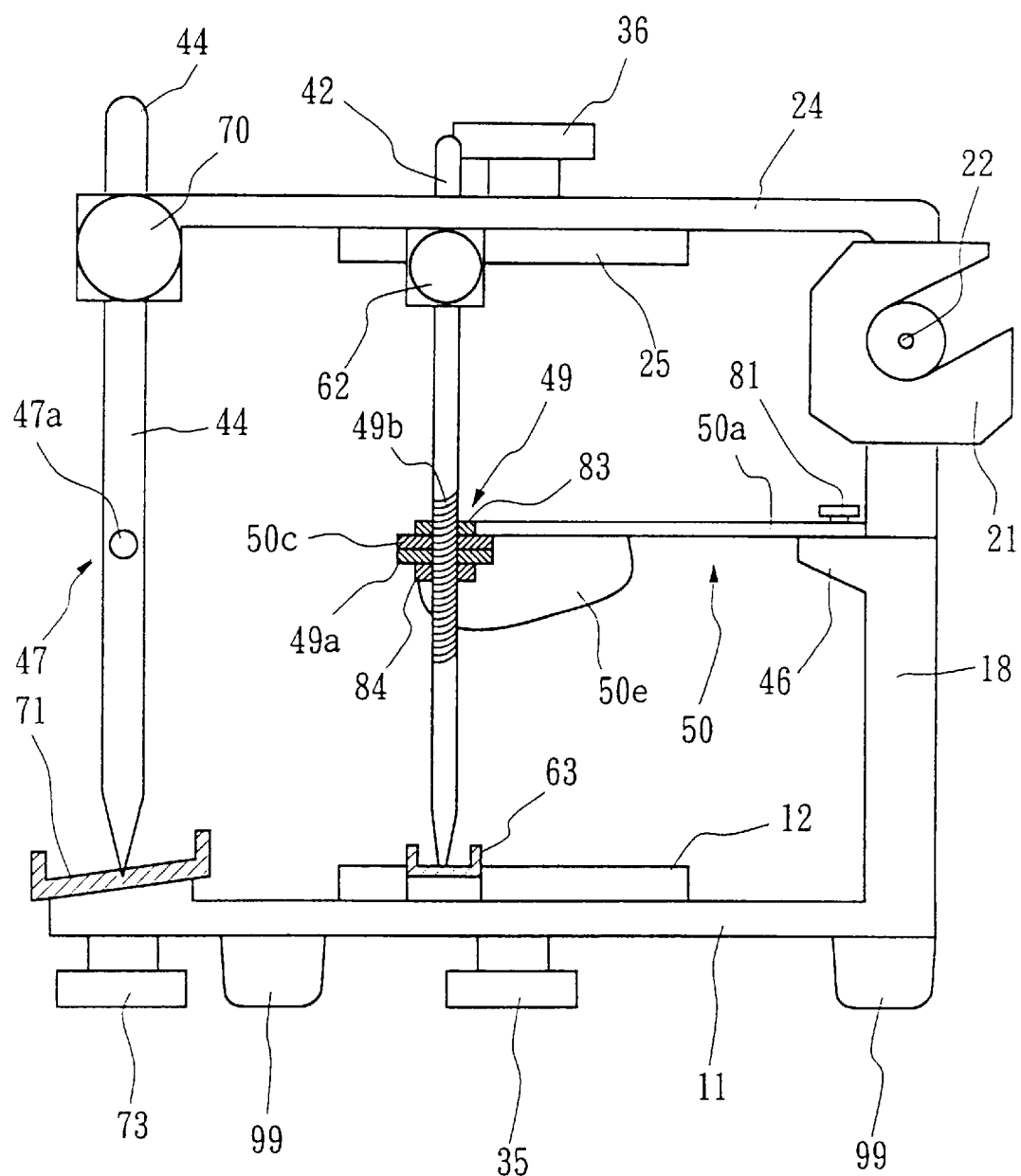
FIG. 8 is a schematic right side view of the denture producing device in a form different from those shown in FIGS. 2 and 6, showing the device in a partially omitted and partially sectioned state.

FIGS. 4 and 8 show an example in which pre-fabricated artificial lower molar teeth as standard teeth in tooth alignment are received in a tooth aligning device. The tooth aligning device 50 is fixed to the holding portion 46 of the support rods 17 and 18 removably with fixing screws 81. In the tooth aligning device 50, four thin plates 50a, 50b, 50c and 50d are combined together in a substantially axial symmetry.

In FIG. 4, two left-hand plate members 50a and 50b and two upper plate members 50c and 50d are respectively connected movably, while two right-hand plate members 50b, 50d are connected immovably. One end of each of the two lower plate members 50a and 50b is removably fixed to the holding portions 46 of the support rods 17 and 18 with fixing screws 81. End portions of the two upper plate members 50c and 50d are fixed to the holding portions 49 of the side pins 41 and 42 removably with fixing screws 83 and 84. Thus, the tooth aligning device 50 is fixed removably to the holding portions 46 of the support rods 17 and 18 and to the holding portions 49 of the side pins 41 and 42.

As shown in FIGS. 4 and 8, receptacle portions 50e and 50f made of rubber for receiving pre-fabricated artificial molar teeth therein are fixed to one-side portions of the two plate members 50a and 50b located on both sides of the tooth aligning device 50. Recesses (not shown) are formed in the rubber receptacle portions 50e and 50f, and pre-fabricated artificial molar teeth are received therein and held elastically.

Figure 2:
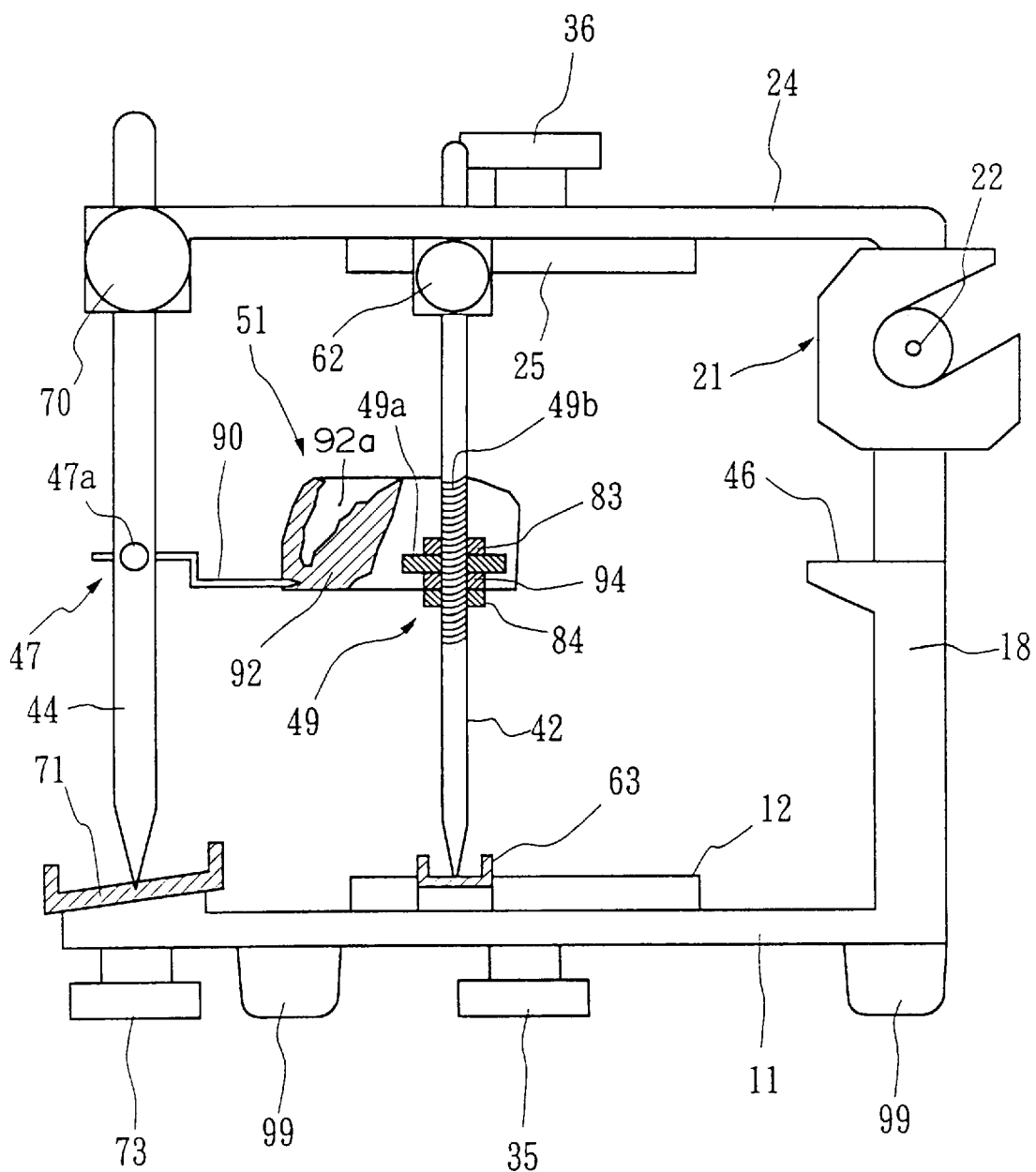
FIG. 2 is a schematic right side view of the denture producing device partially omitted and partially in section.
Figure 3:
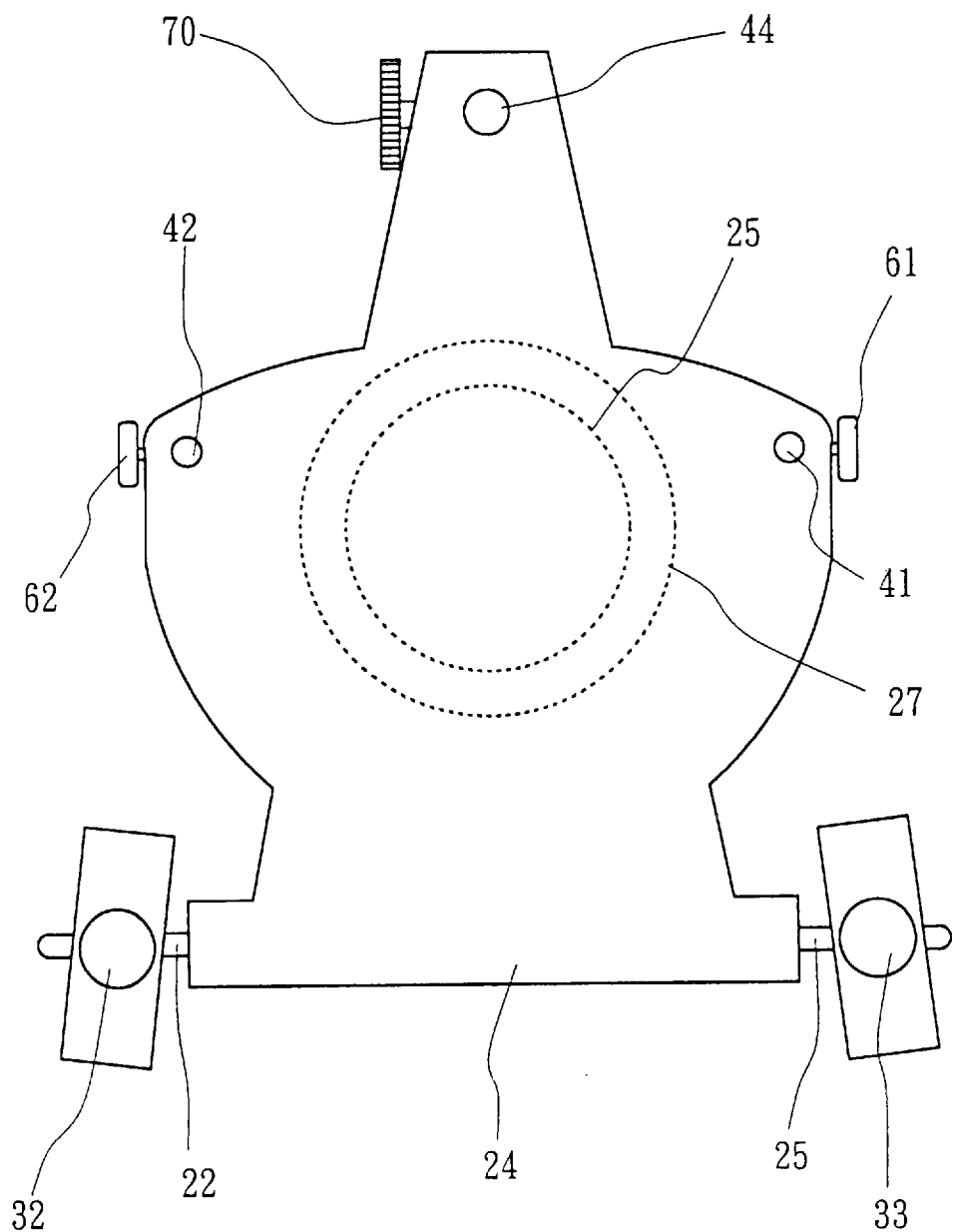
FIG. 3 is a schematic top view of the denture producing device partially omitted.
Figure 5:
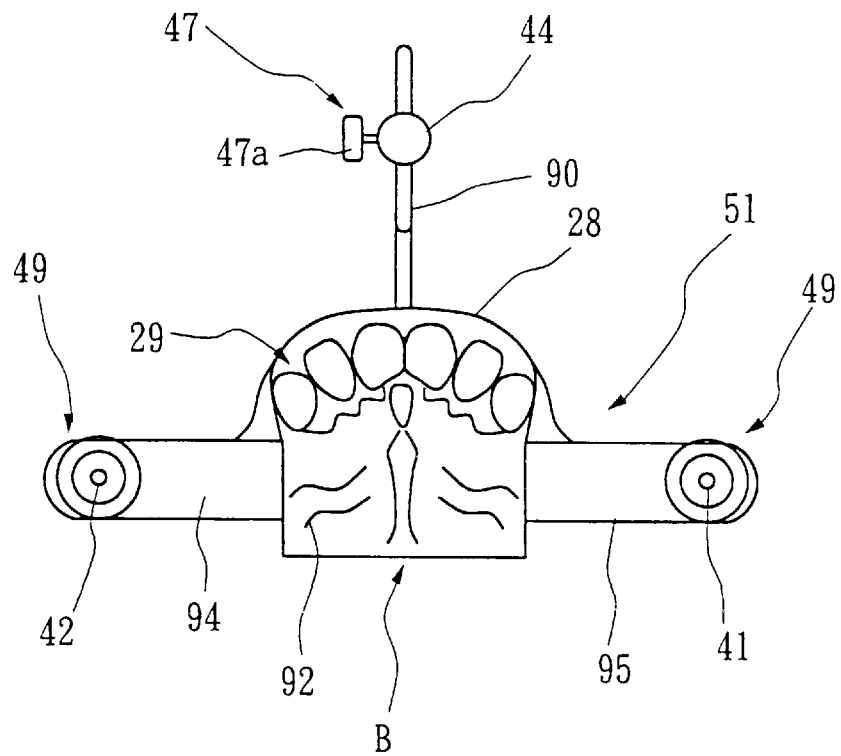
FIG. 5 is a schematic bottom view of an aligning device for maxillary anterior teeth to be used in the denture producing device, showing the aligning device in a partially omitted state.
Figure 6:
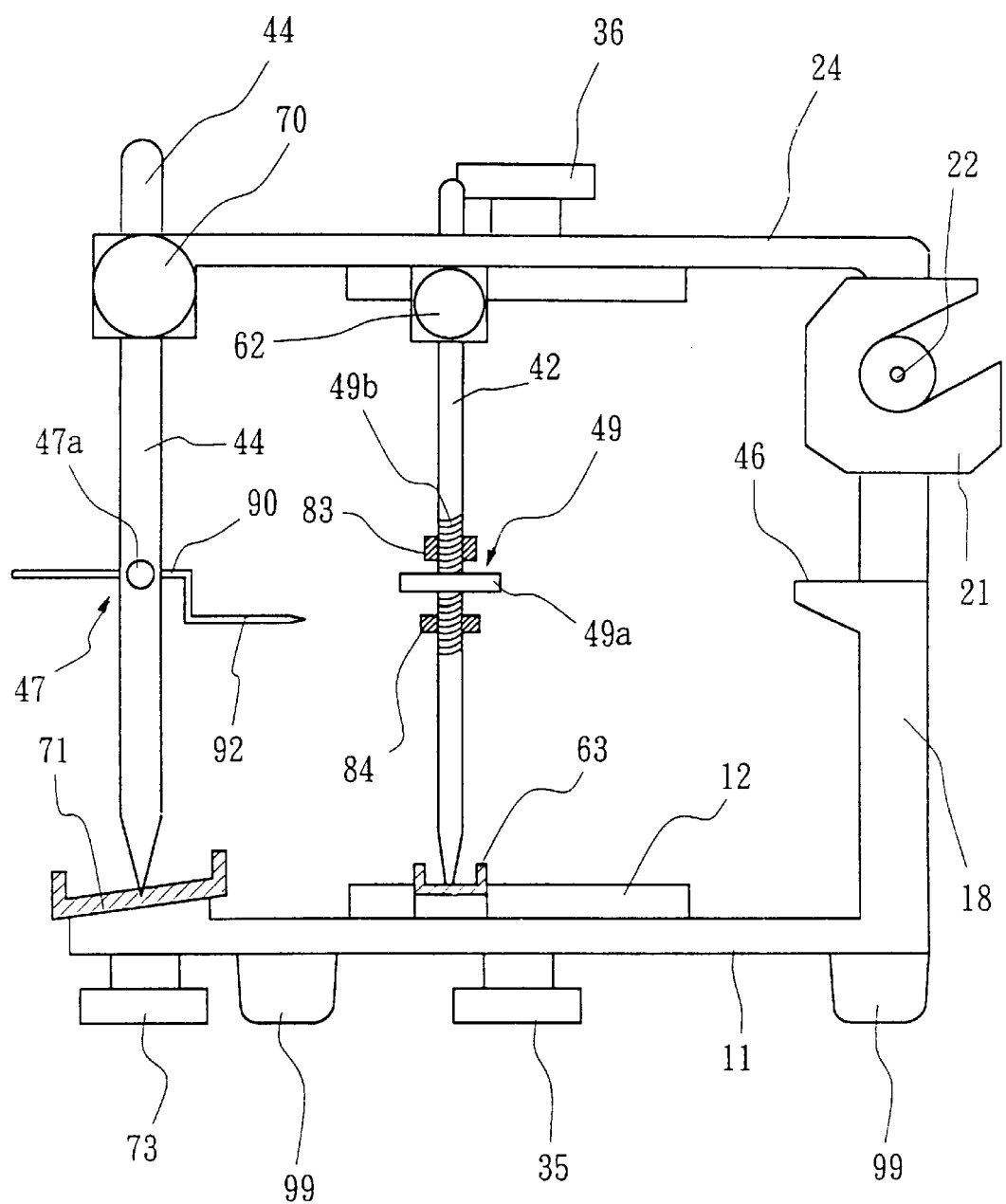
FIG. 6 is a schematic right side view of the denture producing device in a form different from that shown in FIG. 2, illustrating the device in a partially omitted and partially sectioned state.
Figure 7:
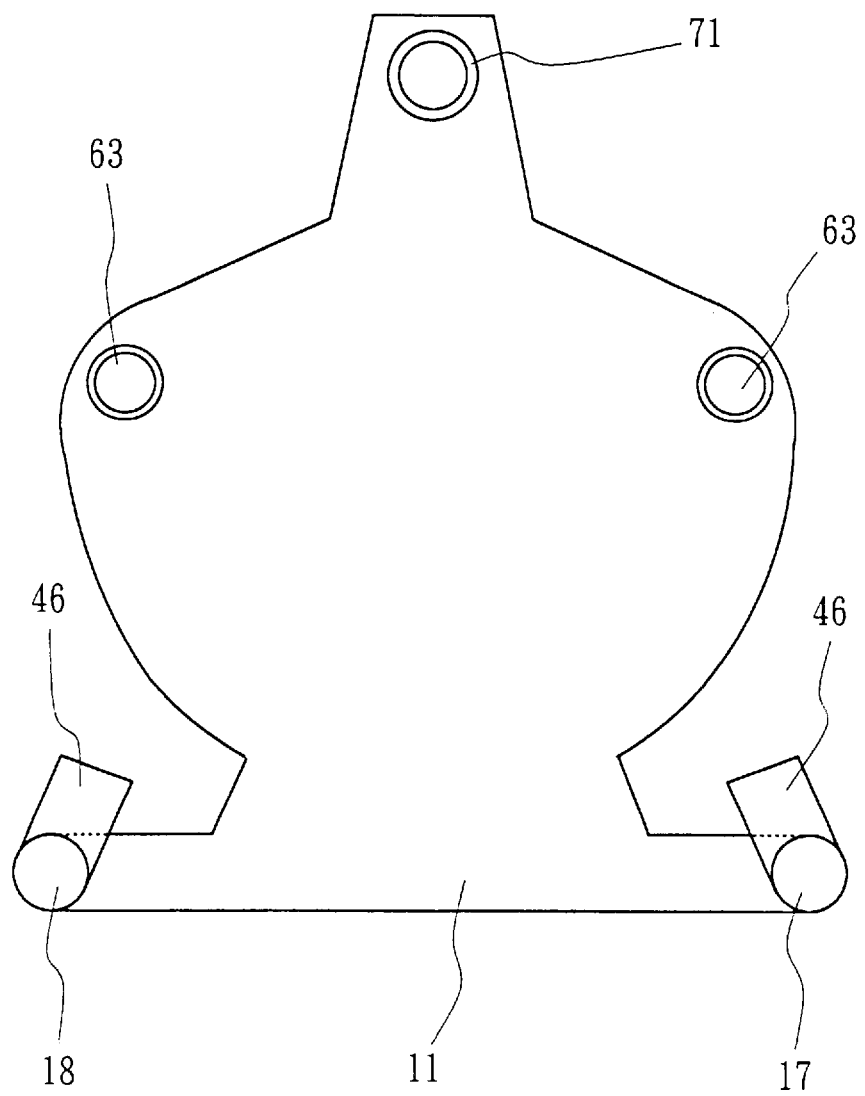
FIG. 7 is a schematic plan view showing, in a partially omitted state, the bottom of the denture producing device illustrated in FIG. 1.

FIGS. 2 and 5 show an example in which pre-fabricated maxillary anterior teeth as standard teeth in tooth alignment are received in a recess 92a formed in a receptacle portion 92 made of rubber. A bar 90 extending horizontally and cranked halfway is mounted at one end portion thereof to the holding portion 47 of the center pin 44 so that its position can be adjusted axially. The opposite end of the bar 90 slightly pierces the receptacle portion 92 of the tooth aligning device 51, as best seen in FIG. 2. Thus, the center pin 44 holds the rubber receptacle portion 92 of the tooth aligning device 51 at a predetermined position through the bar 90.

Further, the receptacle portion 92 of the tooth aligning device 51 is fixed to the holding portions 49 of the side pins 41 and 42 removably with fixing screws 83 and 84 through thin plastic plate members 94 and 95. The two plate members 94 and 95 may be formed integrally with each other. Thus, the side pins 41 and 42 hold the receptacle portion 92 of the tooth aligning device 51 at a predetermined position through the thin plate members 94 and 95.

The bar 90 may be of a structure which fixes the receptacle portion 92 of the tooth aligning device 51, or it may be simply in the shape of a needle (not shown), or it may be in any other shape, with no limitation to the illustrated example, insofar as it can be mounted to the holding portion 47 of the center pin 44.

In the illustrated denture producing device, the pre-fabricated upper anterior teeth 29 as standard teeth in tooth alignment are received in the recess 92a of the receptacle portion 92, the pre-fabricated lower molar teeth as standard teeth in tooth alignment are received in recesses (not shown) formed in the receptacle portions 50e and 50f of the tooth aligning device 50, one of the two aligning devices 50 and 51 is attached to the articulator 10 with the corresponding working model 13, 14, 26, or 27, fixed thereto, then molten wax is flowed into the aligning device 50 or 51 to perform a standard alignment of the upper anterior teeth or lower molar teeth and a partial gum forming for them, and thereafter the other aligning device is mounted. In this case, minor adjustment of curves is performed according to cases for both upper anterior teeth and lower molar teeth if necessary.

In the transition region from the lingual region of the artificial teeth to the gingival region, the gum forming on the palatal or lingual side is performed by the affixing of a pre-fabricated pattern, though not shown.

As shown in FIG. 8, since a pair of side pins 41 and 42 are disposed at right and left outside of the upper jaw of the artificial teeth, even if the center pin 44 at the midline is removed, the occlusal vertical dimension does not change, therefore, the anterior teeth aligning operation and other operations can be done easily even by an unskilled worker.

Figure 9:
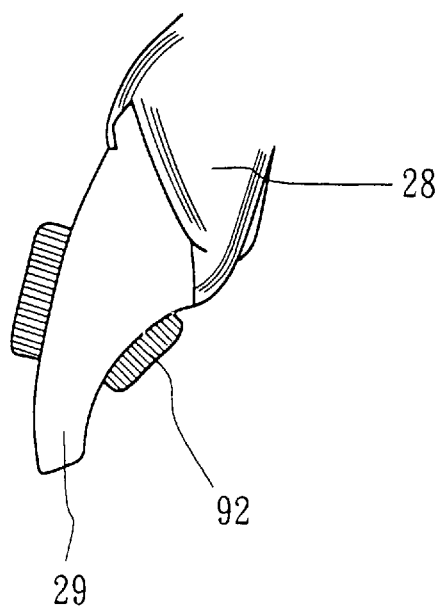
FIG. 9 is a schematic sectioned view showing, in a partially omitted state, a modification of an aligning device for upper anterior teeth to be used in the denture producing device.

FIG. 9 shows a modified example of a tooth aligning device. In this aligning device, a tooth mold made of rubber is in the form of a small ring, and a large number of such rings lie in a row. A series of such rings are fixed with a metallic member (not shown). As in the embodiment illustrated in FIGS. 2 and 5, end portions of that metallic member are fixed to the holding portions of the side pins 41 and 42 removably with fixing screws 83 and 84.

An example of how to use the denture manufacturing device of the invention will be described below.

Articulator Mounting

A wax rim formed by a conventional method and after bite taking is mounted to the articulator 10 of the invention shown in FIG. 1 at a predetermined position, using plaster or the like.

Selection of Artificial Teeth

The form (size and type) of artificial teeth is selected according to the width and diameter of anterior teeth and/or molar teeth.

Mounting Artificial Teeth to Aligning Device

The tooth molds 50e, 50f, and 92, corresponding to the selected artificial teeth are selected, and the artificial teeth 16 and 29 are mounted into the molds.

Then, the anterior teeth are mounted to the anterior teeth aligning device 51 shown in FIG. 5, while the molar teeth are mounted to the molar teeth aligning device 50 shown in FIG. 4.

Mounting Aligning Devices to the Articulator

As to the upper anterior teeth, the anterior teeth region of the wax rim is removed (allowing only the bite plate to remain) and the aligning device 50 is mounted. Thereafter, molten wax is flowed through the clearance between the aligning device 51 and the bite plate to fix the teeth to the bite plate.

Operation for the lower molar teeth is performed after the step of fixing the upper anterior teeth to the bite plate is over. More specifically, the lower wax rim region of the lower molar teeth is removed and the aligning device 50 is mounted. Subsequently, the articulator 10 is reversed and molten wax is flowed through the clearance between the aligning device 50 and the bite plate to fix the teeth to the bite plate.

Aligning Lower Anterior Teeth and Upper Molar Teeth

Align the lower anterior teeth in conformity with the upper anterior teeth by a conventional method.

Align the upper molar teeth in conformity with the lower molar teeth by a conventional method.

Gum Forming of Gingiva around the Artificial Teeth

Patterns of labial and lingual molds for the lower anterior teeth, as well as patterns of buccal and lingual (right and left) molds for the upper molar teeth are affixed to the corresponding portions and the surroundings are arranged with wax.

Gum Forming for the Remaining Portion

Gum forming is performed for the remaining portion to complete a wax denture.

Try-In in the Mouth

This is performed if necessary.

Flasking, Polymerization, and Polishing

These are performed by conventional methods.

Since the mold pattern teeth used in the gum forming step around the artificial teeth stand use several times, they are recovered at the time of dewaxing.

We claim:

1. A denture producing device comprising:

an articulator including a top member for mounting a working model for an upper jaw and a bottom member for mounting a working model for a lower jaw;

a working model for a lower jaw disposed on the bottom member of said articulator;

a pair of support rods disposed on opposite sides of said articulator and connecting said top and bottom members;

a pair of joints respectively disposed on top of said support rods;

a shaft supporting said top member, said shaft having opposing ends respectively supported by said joints, whereby the working model for the upper jaw can be moved relative to the working model for the lower jaw;

a center pin mounted on a line bisecting said articulator; and side pins supported by at least one of said top and bottom members of said articulator and extending between said top and bottom members, each of said side pins and at least one of said center pin and said support rods having a holding fixture for supporting a tooth aligning device, whereby the tooth aligning device may be supported at least at three points by said side pins and said at least one of said center pin and said support rods.

2. A denture producing device according to claim 1 wherein at least two of said holding fixtures are vertically movable.

3. A denture producing device according to claim 1 wherein at least two of said holding fixtures are threadably mounted.

4. A denture producing device according to claim 1 wherein said side pins are fixed to said top member.

* * * * *